(12) United States Patent
de la Poterie et al.

(10) Patent No.: US 6,267,950 B1
(45) Date of Patent: Jul. 31, 2001

(54) AQUEOUS, HIGH VISCOSITY NAIL VARNISH

(75) Inventors: Valérie de la Poterie, Le Chatelet en Brie; Pascale Bernard, Sucy en Brie, both of (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/373,005

(22) Filed: Aug. 12, 1999

(30) Foreign Application Priority Data

Aug. 12, 1998 (FR) .................................... 98 10333

(51) Int. Cl.⁷ .............................. A61K 7/04; A61K 7/00; A61K 7/42
(52) U.S. Cl. ................................ 424/61; 424/401; 424/59
(58) Field of Search ................................ 424/61, 401, 59

(56) References Cited

U.S. PATENT DOCUMENTS

| | | |
|---|---|---|
| 3,639,572 | 2/1972 | Heinrich et al. . |
| 4,108,185 | 8/1978 | Boulogne et al. . |
| 4,158,053 | 6/1979 | Greene et al. . |
| 5,120,529 * | 6/1992 | Koch et al. ............................. 424/61 |
| 5,238,678 | 8/1993 | Shiozawa et al. . |
| 5,538,717 | 7/1996 | La Poterie . |
| 5,571,858 | 11/1996 | de la Poterie et al. .............. 524/462 |
| 5,601,808 | 2/1997 | Mellul et al. . |
| 5,643,581 | 7/1997 | Mougin et al. ...................... 424/401 |
| 5,650,159 | 7/1997 | Lion et al. ........................... 424/401 |
| 5,681,550 | 10/1997 | Rubino . |
| 5,720,943 | 2/1998 | Mougin et al. . |
| 5,753,215 | 5/1998 | Mougin et al. .................... 424/70.1 |

FOREIGN PATENT DOCUMENTS

| | | |
|---|---|---|
| 43 11 039 | 4/1994 | (DE) . |
| 195 21 500 | 6/1996 | (DE) . |
| 143480 * | 9/1984 | (EP) . |
| 0 143 480 | 6/1985 | (EP) . |
| 0 391 322 | 10/1990 | (EP) . |
| 0 418 469 | 3/1991 | (EP) . |
| 0 504 754 | 9/1992 | (EP) . |
| 0 637 600 | 2/1995 | (EP) . |
| 0 648 485 | 4/1995 | (EP) . |
| 0 658 609 | 6/1995 | (EP) . |
| 0 676 451 | 10/1995 | (EP) . |
| 0 680 742 | 11/1995 | (EP) . |
| 0 751 162 | 1/1997 | (EP) . |
| 2 339 393 | 8/1977 | (FR) . |
| 2 399 238 | 3/1979 | (FR) . |
| 2 679 769 | 2/1993 | (FR) . |
| 1 110 240 | 4/1968 | (GB) . |
| 1 180 968 | 2/1970 | (GB) . |
| WO 95/03778 | 2/1995 | (WO) . |
| WO 99/06011 | 2/1999 | (WO) . |

OTHER PUBLICATIONS

G. Fonnum et al., "Associative thickeners. Part I: Synthesis, rhelogy and aggregation behavior", Colloid Polym. Sci., vol. 271, No. 4, Apr. 1993, pp. 380–389.
English language Derwent Abstract of EP 0 504 754.
English language Derwent Abstract of EP 0 637 600.
English language Derwent Abstract of EP 0 658 609.
English language Derwent Abstract of EP 0 751 162.
English language Derwent Abstract of DE 43 11 039.
English language Derwent Abstract of DE 195 21 500.
English language Derwent Abstract of EP 0 418 469.
English language Derwent Abstract of FR 2 399 238.

* cited by examiner

*Primary Examiner*—Thurman K. Page
*Assistant Examiner*—Blessing Fubara
(74) *Attorney, Agent, or Firm*—Finnegan, Henderson, Farabow, Garrett & Dunner, L.L.P.

(57) ABSTRACT

The invention a nail varnish composition comprising an aqueous dispersion of at least one film-forming polymer particle and at least one associative polyurethane in an effective quantity such that the composition has a viscosity of at least 2 Pa.s., at a rotation rate of 100 rpm, at 23° C.

28 Claims, No Drawings

AQUEOUS, HIGH VISCOSITY NAIL VARNISH

The present invention relates to a nail varnish comprising an aqueous dispersion of a film-forming polymer and an associative polyurethane. This varnish can be used for cosmetic or therapeutic treatment of the nails.

Patent applications EP-A-0 143 480, FR-A-2 399 238 and EP-A-0 648 485, the disclosures of each which are specifically incorporated by reference herein, describe fluid nail varnish compositions comprising an aqueous dispersion of film-forming polymer particles.

In water-born nail varnishes, the aqueous phase is routinely thickened using thickening agents. Such thickened compositions readily enable the product to harden outside its packaging without significant loss, thus the product can be evenly distributed over the zone to be treated, or the product can be used in quantities sufficient to obtain the desired cosmetic effect.

However, a such compositions are fluid, it is frequently necessary to apply two coats of the product to obtain a film which covers the nail perfectly, i.e. a film which does not show the ail through the film. Thus the provision of a nail varnish with good coverage properties is desirable.

Further, a nail varnish should have the following qualities: ease of spreading of the varnish on the ail and the production of a glossy, homogeneous film with good cosmetic properties, in particular a smooth appearance.

The aim of he present invention is to provide a nail varnish composition comprising an aqueous dispersion of film-forming polymer particles, which can be easily spread on the nail an which, after application to the nail in a single coat, can result in a perfectly glossy, homogeneous and smooth film covering the nail.

The inventors have discovered that such a composition could be obtained by adjusting the viscosity of the nail varnish composition and by using a particular thickening agent.

Thus the subject of the invention is a nail varnish composition comprising an aqueous dispersion of film-forming polymer particles, characterized in that the composition comprises at least one associative polyurethane in an effective quantity such that the composition has a viscosity of at least 2 Pa.s., measured at 23° C. at a rotation rate of 100 rpm, as explained in greater detail below.

The subject of the invention is also the use of an associative polyurethane in a nail varnish comprising an aqueous dispersion of particles of a film-forming polymer and with a viscosity of at least 2 Pa.s., measured at 23° C. at a rotation rate of 100 rpm.

The subject of the invention is also the use of an associative polyurethane in a nail varnish comprising an aqueous dispersion of film-forming polymer particles, in an effective quantity such that the composition has a viscosity of at least 2 Pa.s., measured a 23° C. at a rotation rate of 100 rpm.

The subject of the invention is also the use of a composition as defined above to produce a glossy and/or homogeneous film and/or a film which gives good coverage.

The subject of the invention is also the use of a composition as defined above as a one-coat varnish.

The subject of he invention is also the use of a composition as defined above as a film-forming varnish.

The subject of the invention is also a cosmetic method or cosmetic and non therapeutic treatment for the nails consisting in applying a composition as defined above to the nails.

The inventors have found that associative polyurethanes can produce remarkable properties in nail varnishes and that other known thickening agents in varnishes with a fluid consistency do not produce these desired rheological or cosmetic properties. For example, clays such as bentonite or montmorillonite have not been found to produce viscosities of over 2 Pa.s.; cellulose polymers such as hydroxyethylcellulose have been found to produce a matt film at the desired viscosities; acrylic type thickening polymers, including associative acrylic polymers, have not been found to produce satisfactory spreading at the desired viscosities.

A nail varnish which should be easy to spread on the nail and which can produce a film with good coverage on application of a single coat may be obtained due to the associative polyurethane and the high viscosity of the composition. Further, the film should be perfect homogeneous and smooth, with no traces of brush strokes. The film obtained after drying should also have a good gloss: the gloss is 80 or more, in particular in the range 80 to 100, measured using a BYK-GARDNER gloss meter at a light beam angle of 60°.

The varnish of the invention allows a thick film to be deposited on the nail in a single coat. Further, the varnish of the invention can be perfectly suitable for use as a film-forming varnish.

The viscosity of the composition of the invention is at least 2 Pa.s. (2000 cps), preferably less than 8 Pa.s. as beyond that, the composition can no longer be applied using a brush. Advantageously, the viscosity of the composition can range from 4 Pa.s. (4000 cps) to 6 Pa.s. (6000 cps).

The viscosity can be measured with a BROOKFIELD DV-II viscometer provided with a No. 3 spindle, at a rotation rate of 100 rpm, at 23° C., the measurement being carried out after 10 minutes rotation (after which period the viscosity and the rate of rotation of the spindle are seen to stabilize). The viscosity could be measured with other suitable viscometers; one skilled in the art will know how to choose rotation rates, spindles, temperature, measurement times, and any other parameter needed to obtain the equivalent to those viscosity values obtained from the BROOKKFIELD DV-II that form part of the present invention. Other viscometers are available from vendors, including, for example, BROOKFIELD, HAAKE, AND RHEOMETRICS.

Associative polyurethanes are nonionic block copolymers comprising in the chain both hydrophilic sequences, which are usually polyoxyethylene-containing, and hydrophobic sequences which can be aliphatic concatenations alone and/or cycloaliphatic concatenations and/or aromatic concatenations.

In particular, these polymers comprise at least two hydrocarbon-containing lipophilic chains containing $C_6$ to $C_{30}$ carbon atoms, separated by a hydrophilic sequence, the hydrocarbon-containing chains possibly being pendent chains or chains at the end of the hydrophilic sequence. In particular, at least one pendent chain can be provided. Further, the polymer can comprise a hydrocarbon-containing chain at one or both ends of a hydrophilic sequence.

The polymers can be in the form of triblock or multiblock block polymers. The hydrophobic sequences can thus be at each end of the chain (for example: a triblock copolymer with a central hydrophilic sequence) or distributed both at the ends and within the chain (multiblock copolymer, for example). The polymers can also be graft or star polymers.

The polymers are preferably triblock copolymers in which the hydrophilic sequence is a polyoxyethylene-containing chain comprising 50 to 1000 oxyethylene groups.

In general, associative polyurethanes comprise a urethane bond between the hydrophilic sequences, hence the origin of the name.

Examples of associative polymers suitable for use in the invention which can be cited are the $C_{16}$-$OE_{120}$-$C_{16}$ polymer sold by HULS (under the trade name Sérad FX1100, a molecule with a urethane function and a weight-average molecular weight of 1300), OE being an oxyethylene moiety. The associative polymer can also be Rheolate 205 with a urea function sold by RHEOX, or Rheolate 208 or 204. These associative polyurethanes are sold in their pure form.

DW 1206B from ROHM & HAAS with a $C_{20}$ alkyl chain and with a urethane bond, sold as 20% dry matter in water, can also be used.

It is also possible to use solutions or dispersions of these polymers, in particular in water or in an aqueous-alcoholic medium. Examples of such polymers which can be cited are Sérad FX1010, Sérad FX1035 and Sérad 1070 sold by HULS, and Rheolate 255, Rheolate 278 and Rheolate 244 sold by RHEOX. It is also possible to use DW1206F and DW1206J, as well as Acrysol RM 184 or Acrysol 44 from ROHM & HAAS, or Borchigel LW44 from BORCHERS.

Particular polymers which can be used in the invention are described in the article by G. Fonnum, J. Bakke and Fk. Hansen—Colloid Polym. Sci. 271, 380.389 (1993), the disclosure of which is incorporated by reference herein.

The composition of the invention comprises at least one associative polyurethane in a quantity sufficient to obtain a composition with the viscosity indicated above. Advantageously, the associative polyurethane can be present in a quantity ranging from 0.5% to 5% by weight with respect to the total composition weight.

Among the film-forming polymers which can be cited for use in the composition of the present invention are synthetic polymers which are free-radical type polymers or polycondensates, polymers of natural origin, and mixtures thereof.

The term "free-radical film-forming polymer" means a polymer obtained by polymerization of unsaturated monomers, in particular ethylenic monomers, each monomer being capable of homopolymerization (in contrast to polycondensates).

The free-radical film-forming polymers can in particular be vinyl polymers or copolymers, in particular acrylic polymers.

The vinyl film-forming polymers can result from polymerization of monomers containing an ethylenic unsaturation containing at least one acid group and/or esters of such acid monomers and/or amides of such acid monomers.

Preferably, anionic free-radical film-forming polymers are used, i.e., monomers with at least one monomer containing an acid group.

Examples of monomers carrying an acid group which can be used are unsaturated $\alpha,\beta$-ethylenic carboxylic acids such as acrylic acid, methacrylic acid, crotonic acid, maleic acid and itaconic acid. Preferably, (meth)acrylic acid and crotonic acid are used, even more preferably, (meth)acrylic acid is used.

The acid monomer esters are advantageously chosen from esters of (meth)acrylic acid (also known as (meth) acrylates), in particular alkyl (meth)acrylates, in particular of $C_1$–$C_{20}$ alkyl, preferably $C_1$–$C_8$, aryl (meth)acrylates, in particular of $C_6$–$C_{10}$ aryl, and hydroxyalkyl (meth)acrylates, in particular of $C_2$–$C_6$ hydroxyalkyl.

The alkyl (meth)acrylates which may be mentioned include methyl methacrylate, ethyl methacrylate, butyl methacrylate, isobutyl methacrylate, 2-ethylhexyl methacrylate and lauryl methacrylate.

The hydroxyalkyl (meth)acrylates which may be mentioned include hydroxyethyl acrylate, 2-hydroxypropyl acrylate, hydroxyethyl methacrylate and 2-hydroxypropyl methacrylate.

The aryl (meth)acrylates which may be mentioned include benzyl acrylate and phenyl acrylate.

Alkyl (meth)acrylates are particularly preferred (meth) acrylic acid esters.

In accordance with the present invention, the alkyl group of the esters can either be fluorinated or perfluorinated, i.e., part or all of the hydrogen atoms of the alkyl group are substituted by fluorine atoms.

Examples of acid monomer amides which can be cited are (meth)acrylamides, in particular N-alkyl (meth) acrylamides, more particularly of $C_2$–$C_{12}$ alkyl. The N-alkyl (meth)acrylamides which may be mentioned include N-ethylacrylamide, -t-butylacrylamide and N-t-octylacrylamide.

Representative film-forming vinyl polymers can also result from homopolymerization or copolymerization of monomers selected from vinyl esters and styrene monomers. In particular, such monomers can be polymerized with acid monomers and/or their esters and/or their amides, such as those mentioned above.

Examples of vinyl esters which may be mentioned are vinyl acetate, vinyl neodecanoate, vinyl pivalate, vinyl benzoate and vinyl t-butylbenzoate.

Examples of styrene monomers which may be mentioned are styrene and $\alpha$-methylstyrene.

The list of monomers given is not limiting and it is possible to use any monomer which is known to the skilled person which falls into the categories of acrylic and vinyl monomers (including monomers modified by a silicon-containing chain).

The film-forming acrylic polymers suitable for use in the invention and which may be mentioned include those sold under the trade names NEOCRYL XK-90®, NEOCRYL A-1070®, NEOCRYL A-1090®, NEOCRYL BT-62®, NEOCRYL A-1079® and NEOCRYL A-523® from ZENECA, and DOW LATEX 432® from DOW CHEMICAL.

Thus, polycondensates which may be mentioned as being suitable for use as film-forming polymers include anionic, cationic, non ionic or amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The polyurethane can, for example, be an aliphatic, cycloaliphatic or aromatic polyurethane, polyurea/urethane or polyurea copolymer comprising, alone or as a mixture:

at least one sequence of aliphatic and/or cycloaliphatic and/or aromatic polyester origin, and/or at least one branched or unbranched silicone sequence, for example polydimethylsiloxane or polymethylphenylsiloxane, and/or at least one sequence comprising fluorinated groups.

The film-forming polyurethanes as defined in the invention can also be obtained from branched or unbranched polyesters, or from alkyds containing labile hydrogen atoms, which are modified by reaction with a diisocyanate and a difunctional organic compound (for example dihydro, diamino or hydroxyamino) also containing either a carboxylic acid or carboxylate group, or a sulphonic acid or sulphonate group, or else a neutralizable tertiary amine group or a quaternary ammonium group.

The film-forming polyurethane can be selected from polyester-polyurethanes and polyether-polyurethanes, preferably from anionic polyester-polyurethanes and anionic polyether-polyurethanes.

Advantageously, the aqueous dispersion of film-forming polymer particles which can be used is an aqueous dispersion of an anionic polyester-polyurethane wherein the polyurethane particle size is in the range 2 to 100 nanometres (nm) and/or wherein the hardness of a film obtained after drying a 300 μm thick coat (before drying) of an aqueous dispersion containing 28% dry matter of said polyurethane particles for 24 hours at 30° C. and at 50% relative humidity is in the range 50 to 300 seconds.

The film hardness is measured in accordance with ASTM standard D-4366-95, or French standard NF-T 30-016 (October 1981), the disclosures of each which are incorporated by reference herein, using a Persoz pendulum.

These aqueous dispersions are perfectly suitable for the production of a film-forming varnish.

Such anionic polyester-polyurethane aqueous dispersions are in particular sold under the trade names "AVALURE UR 405®", "AVALURE UR 410®" and "SANCURE 2060®" by GOODRICH.

As the aqueous dispersion of film-forming polymer particles, it is also possible to use anionic polyether-polyurethane aqueous dispersions such as those sold under the trade names "SANCURE 878®" by GOODRICH or "NEOREZ R 970®" by ICI.

Polyesters, polyesteramides, fatty chain polyesters, polyamides and epoxyester resins are also polycondensates which can be used as the film-forming polymer.

The polyesters can be obtained in known fashion by polycondensation of dicarboxylic acids with polyols, in particular diols.

The dicarboxylic acid can be aliphatic, alicyclic or aromatic. Examples of such acids which may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers can be used alone or as a combination of at least two dicarboxylic acid monomers. Of these monomers, phthalic acid, isophthalic acid and terephthalic acid are preferably selected.

The diol can be selected from aliphatic, alicyclic and aromatic diols. Preferably, a diol selected from the following is used: ethylene glycol, diethylene glycol, triethylene glycol, 1,3-propanediol, cyclohexanedimethanol, 4-butanediol. Other suitable polyols which may be used are glycerol, pentaerythritol, sorbitol or trimethylolpropane.

The polyesteramides can be obtained in a manner analogous to that for polyesters, by polycondensation of dibasic acids with diamines or amino alcohols. Suitable diamines are ethylenediamine, hexamethylenediamine and meta- or paraphenylenediamine. A suitable amino alcohol is monoethanolamine.

The polyester can also comprise at least one monomer carrying at least one —$SO_3M$ group where M represents a hydrogen atom, an ammonium ion $NH_4^+$ or a metal ion, such as an $Na^+$, $Li^+$, $K^+$, $Mg^{2+}$, $Ca^{2+}$, $Cu^{2+}$, $Fe^{2+}$, or $Fe^{3+}$ ion. In particular, a difunctional aromatic monomer comprising such an —$SO_3M$ group can be used.

The aromatic nucleus of the difunctional aromatic monomer also carrying an —$SO_3M$ group as described above can be selected, for example, from benzene, naphthalene, anthracene, biphenyl, oxybiphenyl, sulphonylbiphenyl, and methylenebiphenyl nuclei. Examples of difunctional aromatic monomers also carrying an —$SO_3M$ group which can be cited are: sulphoisophthalic acid, sulphoterephthalic acid, sulphophthalic acid, 4-sulphonaphthalene-2,7-dicarboxylic acid.

Preferably, the compositions of the invention use isophthalate/sulphoisophthalate based copolymers, more particularly copolymers obtained by condensation of diethylene glycol, cyclohexanedimethanol, isophthalic acid and sulphoisophthalic acid. Such polymers are sold, for example, under the trade name Eastman AQ by Eastman Chemical Products.

The polymers of natural origin, which may be modified, can be selected from shellac resin, sandarac gum, dammar resins, elemi resins, copal resins, water-insoluble cellulose polymers and mixtures thereof.

Polymers resulting from free-radical polymerization of at least one free-radical monomer within and/or partially on the surface of pre-existing particles of at least one polymer selected from the group formed by polyurethanes, polyureas, polyesters, polyesteramides and/or alkyds can also be cited. These polymers are generally termed hybrid polymers.

The dispersion comprising at least one film-forming polymer can be prepared by the skilled person on the basis of general knowledge.

The particle size of the aqueous polymer dispersions can be preferably in the range 10 to 500 nm, more preferably in the range 20 to 300 nm.

The polymer in aqueous dispersion can be present in the composition of the invention preferably in an amount in the range 1% to 50% by weight, more preferably in the range 5% to 45% by weight of dry matter of film-forming polymers with respect to the total composition weight.

To improve the film-forming properties of the composition of the invention, the composition can contain plasticizers and/or coalescing agents which are well known to the skilled person.

Further, the composition of the invention can contain additives which are in routine use in cosmetic compositions, in particular in topical cosmetic compositions. Examples of additives are colorants, pigments, nacres, lakes, anti-UV agents, preserving agents, surfactants, spreading agents, fragrances and moisturizers. Clearly, the skilled person will be careful to select these optional additive or additives and/or their quantity such that the advantageous properties of the composition of the invention are not or are not substantially altered by the envisaged addition, thus enabling a composition with the viscosity indicated above to be produced.

The composition of the invention can be applied to natural or false nails.

Examples illustrating the present invention without in any way limiting its scope will now be given.

For each composition, the viscosity was measured at 23° C., using a BROOKFIELD DVII viscometer provided with a No. 3 spindle, at a rotation rate of 100 rpm; the measurement was taken after 10 minutes of rotation.

EXAMPLE 1

A nail varnish with the composition below was prepared by simple mixing at room temperature:

| | |
|---|---|
| aqueous dispersion of anionic polyester-polyurethane, containing 35% dry matter (AVALURE UR 405 from GOODRICH) | 47 g |
| aqueous dispersion of acrylate copolymer, containing 44% dry matter | 15 g |
| associative polyurethane in aqueous solution, containing 44% dry matter (BORCHIGEL LW 44 from BORCHERS) | 1.5 g |
| pigments | 1 g |
| plasticizer | 2 g |
| water qs | 100 g |

The viscosity of the composition was 4.5 Pa.s.

It was shown that the varnish applies easily to the nail to produce a smooth, homogeneous and glossy film after application of a single coat, which did not have any brush marks and which covered the nail perfectly.

EXAMPLE 2

A nail varnish with the composition below was prepared:

| | |
|---|---|
| aqueous dispersion of anionic polyester-polyurethane, containing 35% dry matter (AVALURE UR 405 from GOODRICH) | 45 g |
| aqueous dispersion of acrylate copolymer, containing 44% dry matter | 25 g |
| associative polyurethane (Serad FX1100 from SERVO HÜLS) | 0.7 g |
| pigments | 1 g |
| plasticizer | 2 g |
| water qs | 100 g |

The viscosity of the composition was 5.2 Pa.s.

It was shown that the varnish applies easily to the nail to produce a smooth, homogeneous and glossy film after application of a single coat, which did not have any brush marks and which covered the nail perfectly.

EXAMPLES 3 TO 8

Comparative

A film-forming base with the composition below was prepared:

Base:

| | |
|---|---|
| aqueous dispersion of anionic polyester-polyurethane, containing 35% dry matter (AVALURE UR 405 from GOODRICH) | 62.1 g |
| aqueous dispersion of acrylate copolymer, containing 44% dry matter | 19.9 g |
| ethanol | 4.1 g |
| plasticizers | 4.8 g |
| coalescing agent | 1.8 g |
| spreading agent | 0.4 g |
| preserving agents qs | |
| pigments | 1 g |
| pigmenting paste | 2 g |
| water qs | 100 g |

Six nail varnishes with the compositions given in the table below (base+thickening agent) were prepared the cosmetic qualities of the varnishes deposited in a single coat were then studied: the gloss of the film obtained after drying was measured and the appearance of the film and that of the finished applied varnish were evaluated.

The following results were obtained:

| Example | 3 | 4 | 5 | 6 | 7 (NI) | 8 (NI) |
|---|---|---|---|---|---|---|
| Base | 96.1 g | 92.9 g | 97.3 g | 97.2 g | 96.1 g | 96.6 g |
| Thickening agent | 0.8 g E1 | 2 g E2 | 0.6 g E3 | 0.7 g E4 | 0.5 g E5 | 0.4 g E6 |
| Viscosity (Pa.s.) | 4.01 | 3.76 | 4.43 | 4.54 | 3.68 | 3.73 |
| Gloss | 89 | 87 | 87 | 88 | 74 | 14 |
| Appearance of the film | Smooth | Smooth | Smooth | Smooth | Not very Smooth | Non-uniform |
| Finished applied nail varnish | Correct | Correct | Correct | Correct | Trace of brush-stroke | Non-uniform |

NI: not in accordance with the invention.

Thickening agents: the amount given is the dry matter.
E1: Borchigel LW 44 from BORCHERS
E2: Serad 1070 from SERVO HÜLS
E3: Rheolate 205 from RHEOX
E4: Serad FX 1100 from SERVO HÜLS
E5: Acrysol 33 acrylic copolymer from ROHM & HAAS
E6: Thixol 53L acrylic copolymer from COATEX.

The gloss was measured for a moist film 300 $\mu$m thick deposited on a contrast card then kept for 24 hours in an atmosphere with 50% relative humidity. The measurement was carried out using a BYK-GARDNER gloss meter with a light beam angle of 60°.

It was thus seen that only compositions 3 to 6 of the invention enabled a glossy, smooth film to be obtained with no traces of brush strokes.

Composition 7 (not in accordance with the invention) produced a less glossy film which was not very smooth and which showed traces of brush strokes.

Composition 8 (not in accordance with the invention) produced a non-uniform film and the appearance of the finished applied varnish was not very satisfactory.

What is claimed is:

1. A nail varnish composition comprising an aqueous dispersion of at least one film-forming polymer particle and at least one associative polyurethane in an effective amount such that said composition has a viscosity of at least 2 Pa.s., at a rotation rate of 100 rpm, at 23° C.

2. The composition according to claim 1, wherein the viscosity of said composition is less than 8 Pa.s.

3. The composition according to claim 1, wherein the viscosity of said composition ranges from 4 Pa.s. to 6 Pa.s.

4. The composition according to claim 1, wherein said at least one associative polyurethane comprises at least one polyoxyethylene hydrophilic sequence.

5. The composition according to claim 1, wherein said at least one associative polyurethane comprises at least one hydrophobic sequence chosen from aliphatic concatenations, cycloaliphatic concatenations and aromatic concatenations.

6. The composition according to claim 5, wherein said at least one hydrophobic sequence comprises at least two hydrocarbon lipophilic chains separated by a hydrophilic sequence.

7. The composition according to claim 6, wherein said at least two hydrocarbon lipophilic chains comprise $C_6$ to $C_{30}$ carbon atoms.

8. The composition according to claim 6, wherein said at least two hydrocarbon lipophilic chains are pendent chains or chains at the end of said hydrophilic sequence.

9. The composition according to claim 8, wherein at least one of said pendent chains are provided.

10. The composition according to claim 8, wherein said at least two hydrocarbon lipophilic chains are located at one or both ends of the hydrophilic sequence.

11. The composition according to claim 1, wherein said at least one associative polyurethane is a triblock polymer or a multiblock polymer.

12. The composition according to claim 11, wherein said at least one associative polyurethane is a triblock copolymer comprising a central hydrophilic sequence.

13. The composition according to claim 1, wherein there are hydrophobic sequences at both ends of the chain and within the chain of said at least one associative polyurethane.

14. The composition according to claim 1, wherein said at least one associative polyurethane is a triblock copolymer comprising a hydrophilic sequence, wherein said hydrophilic sequence is a polyoxyethylene chain comprising 50 to 1000 oxyethylene groups.

15. The composition according to claim 1, wherein said at least one associative polyurethane is present in an amount ranging from 0.5% to 5% by weight with respect to the total of the composition weight.

16. The composition according to claim 1, wherein said at least one film forming polymer is chosen from free radical polymers, polycondensates, and polymers of natural origin.

17. The composition according to claim 1, wherein said aqueous dispersion of at least one film forming polymer particle is an aqueous dispersion of anionic polyester-polyurethane and further wherein said composition contains a 300 μm thick coat of said aqueous dispersion comprising 28% dry matter of said polyester-polyurethane particles having, as measured for 24 hours at 30° C. and 50% relative humidity, a hardness, after drying, ranging from 50 to 300 seconds.

18. The composition according to claim 1, wherein said at least one associative polyurethane is chosen from polycondensates chosen from polyesters, polyesteramides, fatty chain polyesters, polyamides and expoxy resins.

19. The composition according to claim 16, wherein said polymers of natural origin are chosen from shellac resin, sandarac gum, dammar resins, elemi resins, copal resins, water-insoluble cellulose polymers and mixtures thereof.

20. The composition according to claim 1, wherein said at least one film forming polymer is present in an amount ranging from 1% to 50% by weight of dry matter with respect to the total composition.

21. The composition according to claim 1, wherein said at least one film forming polymer is present in an amount ranging from 5% to 45% by weight of dry matter with respect to the total composition.

22. The composition according to claim 1, wherein said composition further comprises at least one additive chosen from plasticizers, coalescing agents, colorants, pigments, nacres, lakes, anti-UV agents, preserving agents, surfactants, spreading agents, fragrances and moisturizers.

23. The composition according to claim 1, wherein said composition has a gloss of at least 80 when measured using a gloss meter at a light beam angle of 60°.

24. The composition according to claim 1, wherein said composition has a gloss ranging from 80 to 100 when measured using a gloss meter at a light beam angle of 60°.

25. The composition according to claim 1, wherein said at least one associative polyurethane is a block copolymer.

26. A nail varnish composition comprising (i) an aqueous dispersion of at least one film-forming particle and (ii) at least one associative polyurethane in an effective amount such that said composition has a viscosity of at least 2 Pa.s., at a rotation rate of 100 rpm, at 23° C., wherein said at least one associative polyurethane is chosen from block copolymers comprising hydrophilic and hydrophobic sequences.

27. A method of applying a nail varnish, comprising applying a nail varnish composition to nails, wherein said composition comprises:

an aqueous dispersion of at least one film-forming polymer particle and at least one associative polyurethane in an effective quantity such that said composition has a viscosity of at least 2 Pa.s., at a rotation rate of 100 rpm, at 23° C.

28. A method according to claim 27, comprising applying one coat of a nail varnish composition to nails, wherein said composition comprises:

an aqueous dispersion of at least one film-forming polymer particle and at least one associative polyurethane in an effective quantity such that said composition has a viscosity of at least 2 Pa.s., at a rotation rate of 100 rpm, at 23° C.

* * * * *